United States Patent [19]

Scholz et al.

[11] Patent Number: 4,774,937

[45] Date of Patent: * Oct. 4, 1988

[54] CURABLE RESIN COATED SHEET HAVING REDUCED TACK

[75] Inventors: Matthew T. Scholz; Dennis C. Bartizal, both of Woodbury; Katherine E. Reed, Stillwater; Wayne E. Larson; Dean A. Ersfeld, both of Maplewood, all of Minn.; Timothy C. Sandvig, Woodville, Wis.; Richard S. Buckanin, Woodbury, Minn.

[73] Assignee: Minnesota Mining and Manufacturing Company, St. Paul, Minn.

[ * ] Notice: The portion of the term of this patent subsequent to May 22, 2004 has been disclaimed.

[21] Appl. No.: 928,260

[22] Filed: Nov. 6, 1986

Related U.S. Application Data

[63] Continuation of Ser. No. 784,671, Oct. 4, 1985, Pat. No. 4,667,661.

[51] Int. Cl.$^4$ .................. A61L 15/07; A61F 5/04; A61F 13/04; B32B 17/04
[52] U.S. Cl. .................. 128/90; 29/402.09; 138/141; 156/187; 156/189; 156/94; 242/7.22; 427/407.3; 427/412; 428/36; 428/229; 428/230; 428/251; 428/253; 428/254; 428/266; 428/268; 428/273; 428/290; 428/423.1; 428/425.5; 428/425.6; 428/913
[58] Field of Search .............. 128/90; 427/407.3, 412; 428/229, 230, 251, 253, 254, 266, 268, 273, 290, 423.1, 425.5, 425.6, 913

[56] References Cited

U.S. PATENT DOCUMENTS

| | | | |
|---|---|---|---|
| 3,043,298 | 7/1962 | Brickman | 128/91 |
| 3,089,486 | 5/1963 | Pike | 128/90 |
| 3,373,741 | 3/1968 | Hill et al. | |
| 3,420,231 | 1/1969 | Edenbaum | 428/906 |
| 3,630,194 | 12/1971 | Boardman | 128/90 |
| 3,763,858 | 10/1973 | Buese | 128/156 |
| 3,847,722 | 11/1974 | Kistner | |
| 4,100,122 | 7/1911 | Kent | |
| 4,288,479 | 9/1981 | Brack | 428/252 |
| 4,383,079 | 5/1983 | Gasper et al. | 524/767 |
| 4,411,262 | 10/1983 | Von Bonin et al. | 128/90 |
| 4,414,275 | 11/1983 | Woods | 428/252 |
| 4,433,680 | 2/1984 | Yoon | 128/90 |
| 4,454,873 | 6/1984 | Laufenberg et al. | 128/90 |
| 4,502,479 | 3/1985 | Garwood et al. | 128/90 |
| 4,609,578 | 9/1986 | Reed | 428/76 |
| 4,667,661 | 5/1987 | Scholz et al. | 428/229 |

FOREIGN PATENT DOCUMENTS

| | | |
|---|---|---|
| 0086621 | 8/1983 | European Pat. Off. . |
| 0094222 | 11/1983 | European Pat. Off. . |
| 2021128 | 11/1979 | United Kingdom . |
| 2092606 | 8/1982 | United Kingdom . |

*Primary Examiner*—James C. Cannon
*Attorney, Agent, or Firm*—Donald M. Sell; Dale E. Hulse

[57] ABSTRACT

A curable resin coated sheet useful as an orthopedic bandage which has reduced tack is provided. The resin coated sheet is pre-lubricated with a lubricant which is (a) bonded to the resin, (b) added to the resin or applied to the surface of the coated sheet, or (c) a combination of (a) and (b). The lubricant is present in an amount to reduce the kinetic coefficient of friction of a surface of the coated sheet to less than 1.2.

60 Claims, No Drawings

CURABLE RESIN COATED SHEET HAVING REDUCED TACK

This is a continuation of application Ser. No. 784,671, filed Oct. 4, 1985, now U.S. Pat. No. 4,667,661.

FIELD OF THE INVENTION

This invention relates to sheet materials coated with a curable polymeric resin. More particularly, this invention relates to a curable resin coated sheet material useful in preparing an orthopedic bandage.

BACKGROUND OF THE INVENTION

Current synthetic orthopedic casting tapes are produced using curable resins coated on a substrate (fiberglass, polyester, or other synthetic or natural fabric). U.S. Pat. No. 4,411,262 (von Bonin et. al.) and U.S. Pat. No. 4,502,479 (Garwood et. al.) disclose the use of water-curable isocyanate-functional prepolymer in orthopedic casting tapes. After removal of the casting material from the storage pouch, especially after exposure to water used to initiate curing of the prepolymer, these resins are quite tacky until cured. This tackiness makes it difficult to mold the cast to the patient's limb as the resin tends to stick to the protective gloves worn by the cast applier. For example, after the rolls are wrapped but before they harden, some working time is necessary in order to mold the casts to fit the limb. This is accomplished by smoothing the cast with a gloved hand as well as holding the cast at certain points until it hardens. When a roll of tape coated with a tacky resin is used, molding the cast is difficult. The reason for this difficulty is that the glove sticks to the resin and when attempts are made to smooth the cast and form it, the layers of tape pull apart from each other thus requiring reforming of part of the cast.

It is believed that all curable resin coated orthopedic casting materials currently available commercially suffer from the above-noted problems.

U.S. Pat. No. 3,089,486 (Pike) discloses the use of beeswax as a release agent in the formation of an immobilizing orthopedic structure reinforced with a methacrylate polymer.

U.S. Pat. No. 4,100,122 (Kent) discloses the addition of crystalline wax to a mixture of transpolyisoprene and glass fibers to improve the flow characteristics of the composition during preparation, and the use of such compositions in moldable orthopedic devices.

U.S. Pat. No. 3,043,298 (Brickman et al.) discloses the addition of hydroxypropylmethyl-cellulose to a plaster of Paris bandage to be used as an orthopedic cast which gives the plaster of Paris a creamy consistency or texture when wet with water just prior to application.

U.S. Pat. No. 3,763,858 (Buese) discloses a composite material, useful as a surgical, medical, or orthopedic wrapping, which will adhere or cohere to another surface or to itself by the application of moderate pressure either at room temperature or at an elevated temperature and will be substantially nontacky to the touch until the application of such moderate pressure. The composite material comprises a cementitious core having bonded thereto a flexible, open cellular, resilient polymeric protective covering, the core having sufficient softness at the conditions of use to extend through the cells of the protective covering and become available at the outer surface thereof upon application of moderate pressure.

U.S. Pat. No. 3,630,194 (Boardman) discloses an orthopedic bandage comprising a flexible carrier supporting a solid water-soluble vinyl monomer selected from the group consisting of diacetone acrylamide and an isopropyl diacrylamide and mixtures thereof. The bandage is prepared for use by dipping in water in the presence of a catalyst for initiating polymerization of the vinyl monomer and then wrapping the body portion to be immobilized. The patent also discloses the use of inorganic fillers such as calcium sulfate, calcium carbonate, bentonite, or silica, to render the bandage less sticky and moderate any temperature rise during curing.

U.S. Pat. No. 4,454,873 (Laufenburg et al.) discloses an orthopedic cast material having a thermoplastic material and a quantity of polyethylene oxide applied thereto as an anti-block agent to prevent adherence of adjacent convolutions of the cast material when it is in the form of a roll and is immersed in hot water prior to being wrapped on a limb or body part of a patient. The polyethylene oxide can be in the form of a coating on the outer surface of the cast material or in the resin of the cast material. The patent implies that most, if not all of the polyethylene oxide is removed from the casting material when the casting material is removed from the hot water and that talc can be added to the resin to reduce tack.

U.K. Patent Application No. 2,092,606 (Potter et al.) discloses water hardenable splinting banadages comprising a flexible fabric carrying an isocyanate terminated prepolymer having a reaction functionality of two and a catalyst, which bandage is characterised in that the prepolymer is a water absorbing isocyanate terminated prepolymer and the catalyst is water soluble but insoluble in the prepolymer, wherein the prepolymer is derived from an ethylene oxide adduct. The application discloses that the catalyst is preferably an inorganic material which has an alkaline reaction in water, preferably a carbonate or bicarbonate.

A glove lubricant comprised of water, sorbitol, mineral oil and silicone fluid has been sold by 3M Co., St. Paul under the tradename Cast Cream with instructions to apply the lubricant to the gloves of one applying an isocyanate-functional prepolymer coated cast after wrapping of the cast but before molding of the cast to avoid having the exposed casting material adhere to the gloves of the one applying the cast.

SUMMARY OF THE INVENTION

This invention relates to an article comprising a prelubricated curable resin-coated sheet wherein a major surface of the sheet material exhibits a kinetic coefficient of friction of less than about 1.2. The article may be prepared by providing a lubricant at a major surface of the coated sheet wherein said lubricant is comprised of:
  (a) hydrophilic groups which are covalently bonded to the curable resin, or
  (b) an additive which is incompatible with the curable resin, or
  (c) a combination of (a) and (b);
and wherein said lubricant is present in an amount such that the kinetic coefficient of friction of the sheet material is less than about 1.2. The additive lubricants are preferably selected from the group consisting of:
  (i) a surfactant,
  (ii) a polymer comprised of a plurality of hydrophilic groups,
  (iii) a polysiloxane, and
  (iv) mixtures of any of (i), (ii) and (iii).

As discussed hereinafter, the tack exhibited by a surface of a sheet correlates with the kinetic coefficient of friction of the surface such that a reduction in the tack results in reduction of the kinetic coefficient of friction.

This invention also relates to methods of preparing the article described above. More particularly, this invention relates to a method of reducing the tack of a surface of a curable resin coated sheet comprising depositing a layer of a lubricating composition comprised of an additive which is incompatible with the curable resin onto one or more major surfaces of a sheet coated with a curable resin wherein the lubricating composition is present in an amount sufficient to reduce the kinetic coefficient of friction of the major surfaces of the sheet to less than about 1.2 and wherein said layer is deposited before said sheet is wrapped about a substrate. The layer may be deposited onto the surface of the sheet by spraying, by roll coating, or by dipping the sheet into a composition containing the lubricant, e.g., the lubricants that are compatible with water can be added to the water in which the sheet is dipped to effect cure.

This invention also relates to a method of preparing a sheet coated with a curable resin and having reduced tack comprised of coating a sheet with a mixture comprised of:
  (a) a curable resin; and
  (b) an additive which is incompatible with the curable liquid resin;
wherein the amount of the additive is sufficient to reduce the kinetic coefficient of friction of the major surfaces of the sheet to less than about 1.2.

This invention also relates to a method of preparing a sheet coated with a curable resin and having reduced tack comprised of coating a sheet with a curable resin wherein the curable liquid resin is comprised of hydrophilic groups which are covalently bonded thereto and which are present in an amount sufficient to reduce the kinetic coefficient of friction of the major surfaces of the sheet material to less than about 1.2.

The pre-lubricated sheet of this invention exhibits reduced tack prior to and/or during cure of the prepolymer and yet forms a cast which exhibits acceptable strength and lamination of the wrapped layers. As used herein, a pre-lubricated sheet is a sheet which has the lubricant at the surface of the coated sheet prior to wrapping of the sheet about a substrate, including when used as an orthopedic bandage.

DETAILED DESCRIPTION OF THE INVENTION

The embodiments of this invention may be classified into one or more of three classes. In one class, a lubricant is an additive which is chemically unreactive with the curable resin, e.g., a polydialkylsiloxane or an alkyl ionic surfactant as described below. In a second class, the additive is reactive with the resin such that at least a portion of the amount of lubricant may become chemically bonded to the resin, e.g., a hydroxyl-functional surfactant. In a third class, the lubricant is comprised of hydrophilic groups covalently bonded to the resin. Further, these classes are not mutually exclusive in that a single embodiment of this invention may be comprised of a lubricant from all three classes, i.e, a combined lubricant. Indeed, the best mode of this invention is a combined lubricant.

The reactive lubricant additives will vary in the degree to which they react with the resin based on (1) their inherent reactivity, e.g., primary hydroxyl additive lubricants may react faster than secondary hydroxyl lubricants, (2) the length of the period of time from the addition of the reactive additive to the initiation of curing by exposure to water, e.g., the longer the period, the greater the amount of reactive lubricant which will have reacted with the prepolymer to become chemically bonded thereto, and (3) in the case of reactive lubricant additives which are deposited on a curable resin coated sheet the greater the rate of mixing of the reactive lubricant and the curable resin, the greater the amount of lubricant reacted with the resin.

Because of these various factors, it is not convenient to determine precisely to what extent a given reactive lubricant additive applied in a given manner at a given time is chemically bonded to the resin. Accordingly, the disclosure below will not deal with the question of the extent to which a reactive lubricant additive may, in fact, be chemically bonded to the resin. Moreover, because the determination of the extent to which a given reactive lubricant additive is chemically bonded to the resin is unnecessary insofar as the utility of the lubricant in reducing tack is concerned, no distinction will be made below between unreactive and reactive lubricant additives, i.e., the unreactive and reactive lubricant additives will be disclosed together in Section II, below, apart from the bound lubricants disclosed in Section I, below.

The embodiments of the invention which employ a polysiloxane as a lubricant exhibit reduced tack both prior to and after exposure of the prepolymer to water.

The kinetic coefficient of friction of the articles of this invention generally range from about 0.2 to about 1.2, more preferably less than about 0.75 and most preferably less than about 0.4.

One element of this invention is a semi-rigid or flexible sheet upon which a curable resin can be coated to reinforce the sheet when the resin is cured thereon. The sheet is preferably porous such that the sheet is at least partially impregnated with the resin. Examples of suitable sheets are non-woven, woven, or knit fabrics comprised of natural or synthetic fibers. Preferred sheets are knit fiberglass fabrics, and particularly preferred sheets of this type are extensible, heat-set fabrics as disclosed in U.S. Pat. No. 4,609,578, which issued Sept. 2, 1986.

The curable resins useful in this invention are resins which can be used to a coat a sheet material and which can then be cured to reinforce the sheet material. The resin is curable to a crosslinked thermoset state. The preferred curable resins are fluids, i.e., compositions having viscosities between about 5,000 cps and about 500,000 cps, preferably about 10,000 cps to about 100,000 cps.

The resin used in the casting material of the invention is preferably any curable resin which will satisfy the functional requirements of an orthopedic cast. Obviously, the resin must be nontoxic in the sense that it does not give off significant amounts of toxic vapors during curing which may be harmful to either the patient or the person applying the cast and also that it does not cause skin irritation either by chemical irritation or the generation of excessive heat during cure. Furthermore, the resin must be sufficiently reactive with the curing agent to insure rapid hardening of the cast once it is applied but not so reactive that it does not allow sufficient working time to apply and shape the cast. Initially, the casting material must be pliable and formable and should adhere to itself. Then in a short time following completion of cast application, it should become rigid or, at least, semi-rigid, and strong to support loads and stresses to which the cast is subjected by the activities of the wearer. Thus, the material must undergo a change of state from a fluid-like condition to a solid condition in a matter of minutes.

The preferred resins are those cured with water. A number of classes of water-curable resins known in the art are suitable, including polyurethanes, cyanoacrylate esters, and, when combined with moisture sensitive catalysts, epoxy resins and prepolymers terminated at their ends with trialkoxy- or trihalo-silane groups. For example, U.S. Pat. No. 3,932,526 discloses that 1,1-bis(-perfluoromethylsulfonyl)-2-aryl ethylenes cause epoxy resins containing traces of moisture to become polymerized.

Resin systems other than those which are water-curable may be used, although the use of water to activate the hardening of an orthopedic casting tape is most convenient, safe and familiar to orthopedic surgeons and medical casting personnel. The principles disclosed herein regarding the kinetic coefficient of friction of the casting material are applicable to resin systems such as that disclosed in U.S. Pat. No. 3,908,644 in which a bandage is impregnated with difunctional acrylates or methacrylates, such as the bis-methacrylate ester derived from the condensation of glycidyl methacrylate and bisphenol A (4,4'-isopropylidenediphenol). The resin is hardened upon wetting with solutions of a tertiary amine and an organic peroxide. Also, the water may contain a catalyst. For example, U.S. Pat. No. 3,630,194 proposes an orthopedic tape impregnated with acrylamide monomers whose polymerization is initiated by dipping the bandage in an aqueous solution of oxidizing and reducing agents (known in the art as a redox initiator system). The strength, rigidity and rate of hardening of such a bandage is subjected to the factors disclosed herein.

Also suitable ae urethane resins cured by the reaction of a polyisocyanate and a polyol such as those disclosed in U.S. Pat. No. 4,131,114.

The preferred resins for use in the present invention are water-curable, isocyanate-functional prepolymers. Suitable systems of this type are disclosed, for example, in U.S. Pat. No. 4,411,262, and in U.S. Pat. No. 4,502,479. The following disclosure relates primarily to the preferred embodiment of the invention wherein water-curable isocyanate-functional prepolymers are employed as the curable resin.

It is preferred to coat the resin onto the fabric as a polyisocyanate prepolymer formed by the reaction of an isocyanate and a polyol. It is preferred to use an isocyanate which has low volatility such as diphenylmethane diisocyanate (MDI) rather than a more volatile material such as toluene diisocyanate (TDI). Suitable isocyanates include 2,4-toluene diisocyanate, 2,6-toluene diisocyanate, mixtures of these isomers, 4,4'-diphenylmethane diisocyanate, 2,4'-diphenylmethane diisocyanate, mixtures of these isomers together with possible small quantities of 2,2'-diphenylmethane diisocyanate (typical of commercially available diphenylmethane diisocyanate), and aromatic polyisocyanates and their mixtures such as are derived from phosgenation of the condensation product of aniline and formaldehyde. Typical polyols for use in the prepolymer system include polypropylene ether glycols (available from Union Carbide under the tradename Niax TM PPG and from BASF Wyandotte under the tradename Pluracol TM), polytetramethylene ether glycols (Polymeg TM from the Quaker Oats Co.), polycaprolactone diols (Niax TM PCP series of polyols from Union Carbide), and polyester polyols (hydroxyl terminated polyesters obtained from esterification of dicarboxylic acids and diols such as the Rucoflex TM polyols available from Ruco division, Hooker Chemicals Co.). By using high molecular weight polyols, the rigidity of the cured resin can be reduced.

An example of a resin useful in the casting material of the invention uses an isocyanate known as Isonate TM 143L available from the Upjohn Company (a mixture containing about 73% of MDI) and a polypropylene oxide polyol from Union Carbide known as Niax TM PPG725. To prolong the shelflife of the material, it is preferred to include from 0.01 to 1.0 percent by weight of benzoyl chloride or another suitable stabilizer.

The reactivity of the resin once it is exposed to the water curing agent can be controlled by the use of a proper catalyst. The reactivity must not be so great that: (1) a hard film quickly forms on the resin surface preventing further penetration of the water into the bulk of the resin; or (2) the cast becomes rigid before the application and shaping is complete. Good results have been achieved used 4-[2-[1-methyl-2-(4-morpholinyl)ethoxy]ethyl]-morpholine (MEMPE) prepared as described in U.S. Pat. No. 4,705,840, the disclosure of which is incorporated by reference, at a concentration of about 0.05 to about 5 percent by weight.

Foaming of the resin should be minimized since it reduces the porosity of the cast and its overall strength. Foaming occurs because carbon dioxide is released when wter reacts with isocyanate groups. One way to minimize foaming is to reduce the concentration of isocyanate groups in the prepolymer. However, to have reactivity, workability, and ultimate strength, an adequate concentration of isocyanate groups is necessary. Although foaming is less at low resin contents, adequate resin content is required for desirable cast characteristics such as strength and resistance to peeling. The most satisfactory method of minimizing foaming is to add a foam suppressor such as silicone Antifoam A (Dow Corning), or DB-100 silicone fluid (Dow Corning) to the resin. It is especially preferred to use a silicone liquid such as Dow Corning DB-100 at a concentration of about 0.05 to 1.0 percent by weight.

A water-curable isocyanate-functional prepolymer as used herein means a prepolymer derived from polyisocyanate, preferably aromatic, and a reactive hydrogen compound or oligomer. The prepolymer has sufficient isocyanate-functionality to cure upon exposure to water, e.g., moisture vapor or, preferably liquid water.

I. BOUND LUBRICANTS

One aspect of this invention is a sheet, e.g., a scrim, coated with a curable resin wherein one or more hydrophilic groups are chemically bound to the resin. When this orthopedic casting material is brought into contact with water, the hydrophilic group causes the resin to become slippery. This allows for easy application and molding of the cast for the most efficacious fit without the casting material sticking to the gloved hands of the person applying the cast. As noted above, this is advantageous because if the casting material is sticky, application and molding of the cast is difficult. Further, because the hydrophilic groups are chemically bonded to the curable resin, they cannot be leached out by contact with water subsequent to curing. Accordingly, any potential for skin irritation is reduced.

The curable resin containing bound hydrophilic groups can be prepared by a variety of methods. One method relates to the introduction of hydrophilic groups into a curable resin. For example, an aromatic isocyanate-functional prepolymer can be sulfonated with sulfonic acid or its derivatives to obtain a sulfonated isocyanate-functional prepolymer.

A second method relates to the polymerization of monomers comprised of hydrophilic groups to form a curable resin. For example, the preferred resin is an isocyanate-functional prepolymer that is, at least in part, the reaction product of an active hydrogen compound or oligomer with an isocyanate-functional compound or oligomer wherein at least one of the reactants is comprised of at least one hydrophilic group such that the reaction product retains sufficient hydrophilicity to give the prepolymer the desired kinetic coefficient of friction when contacted with water. Preferred prepolymers are prepared from hydroxyl-functional oligomers comprised of hydrophilic groups having repeating units derived from ethylene oxide.

Many hydrophilic functional group prepolymers are suitable for making moldable orthopedic casting materials within the scope of this invention. Preferred isocyanate-functional prepolymers are prepared by reacting a polyisocyanate compound or oligomer, e.g., diphenylmethanediisocyanate, (MDI), with an active hydrogen compound or oligomer comprised of groups selected from the following:

(1) alkali metal salts of sulfated or sulfonated polyesters or polyethers,
(2) quaternary ammonium salts containing carbamates derived from polyesters or polyethers,
(3) alkali metal salts of phosphonated or phosphated polyesters or polyethers, and
(4) polyethylene oxide.

The curing of an isocyanate-functional prepolymer coated sheet is generally initiated by immersion of the sheet in water. Accordingly, the hydrophilicity of the water-curable isocyanate-functional prepolymer should not be so great that the resin composition is very dispersible in water which would allow the resin composition to leach out into the water bath in which the sheet is immersed. Therefore the hydrophilicity of the prepolymer should be such that the prepolymer is not appreciably dispersible, if at all, in water at ambient temperatures. By not appreciably dispersible, it is meant that a roll of curable resin coated sheet when immersed in water and squeezed several times while immersed will retain at least about 70%, more preferably at least about 85%, and most preferably at least about 95% by weight of the resin composition on the sheet. Further, water retained in or absorbed into the cured resin may adversely affect the rigidity of the cured resin and thereby reduce its wet strength. Accordingly, the hydrophilic functionality of the cured resin should be controlled such that excess amounts of water are not retained in, or absorbed into the cured resin. The hydrophilicity of the resin composition can be controlled by choosing prepolymer-forming reactants having sufficiently low hydrophilic group functionality that the reactants are not appreciably dispersible in water or by using amounts of dispersible reactants that are minor compared to the amounts of reactants that are not appreciably dispersible in water. For example, when the prepolymer is prepared from a mixture of an aromatic isocyanate, e.g., 2,2-diphenylmethane diisocyanate (MDI) and one or more polyether polyols having only polyethylene oxide as a hydrophilic group, the amount of polyethylene oxide by weight of the prepolymer should be less than about 15 percent, preferably less than about 10 percent, most preferably less than 6 percent, e.g., 3–4 percent.

Examples 1–6 illustrate embodiments of bound lubricants.

II. ADDITIVE LUBRICANTS

In another aspect of this invention, the lubricant is an additive. The additive is incompatible with the curable resin such that the additive forms a shear layer on the surface of the curable resin. Accordingly, the term "incompatible" as used herein shall mean the ability of any composition to form a shear layer on the surface of a curable resin. Some additives, e.g., the ionic alkyl surfactants form a shear layer when wetted with water. These additives can be mixed with the resin before application of the resin to the sheet, but are preferably deposited on the surfaces of a curable resin coated sheet in an amount sufficient to reduce the kinetic coefficient of friction of the coated sheet during cure.

The additive is deposited on the surface of the casting material prior to wrapping about a substrate in any manner which will deposit the amount necessary to reduce the kinetic coefficient of friction to the desired level. The additive is preferably coated on the surfaces of the casting material prior to the packaging thereof, but it may be applied just prior to the wrapping of the casting material. In particular, some additives may be added to a water bath in which the casting material may be immersed to activate the curing of the prepolymer in an amount sufficient to deposit the desired amount of lubricant on the surfaces of the casting material.

The additive lubricants will be discussed hereinbelow as follows:

A. Polysiloxanes
B. Surfactants and Polymers Consisting of Hydrophilic Groups
 1. Ionic Alkyl, Aryl, Aralkyl Surfactants
 2. Polyethoxylated Surfactants
  a. Polyethoxylated Alcohols
  b. Block Copolymers of Propylene Oxide and Ethylene Oxide
 3. Ionic Derivatives of Polyethoxylated Alcohols.

A. Polysiloxanes

Two classes of hydrophobic materials were initially evaluated as lubricants: organic based oils and waxes and silicone based fluids. Of those materials evaluated only those compounds which are essentially immiscible with the resin maintained a lubricating feel after being stored for longer than a few days. Materials such as corn oil; mineral oil; and hydrocarbons such as hexadecane and motor oil did give a non-tacky and even slippery feeling surface which allowed easy application and moldability of the casting tape to the patient, but the effect was transient. On the average, the slippery effect induced by these materials lasted only a day to a week apparently due to dissolution of the lubricant into the resin. Compounds such as lanolin, when applied to the surface of the coated tape in the molten state did remain on the surface of the resin for an extended period of time and did reduce the tackiness of the resin, but also affected the cast detrimentally by reducing the lamination of the casting material.

Unlike the materials discussed above, the silicone based fluids dramatically reduced the tackiness of the resin and surprisingly did not affect the other properties of the cast and even at elevated temperatures remained on the surface of the resin and remained slippery.

Accordingly, this aspect of the invention relates to the use of lubricating silicone fluids which are generally non-irritating to skin in order to reduce the tackiness of curable liquid resin coated casting tapes. The fluids are preferably applied to both major surfaces at 0.9–9.0 g/m² resulting in a casting tape which is easy to apply and mold to a patient's limb. The silicone fluids in the amounts stated above do not adversely affect the physical properties of the cast, and many are safe for use on the skin.

Specifically, the use of the following silicone based compounds is contemplated:

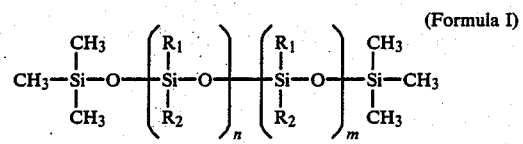

(Formula I)

$R_1$ and $R_2$ may independently be: alkyl ($C_1$–$C_{16}$) chosen independently from: optionally substituted alkyl, optionally substituted aryl, optionally substituted aralkyl, unsaturated alkyl, alkoxy, provided that $R_1$ and $R_2$ are of short enough chain length relative to n and to prevent dissolution of the silicone compound in the resin, m and n are integers, the sum of which range from about 15–800. This value depends on the exact nature of $R_1$ and $R_2$ and the range given is reflective of current commercially available compounds.

Alternatively, the polysiloxane may be terminated with a nonsiloxane moiety. Such polysiloxanes have the following structure:

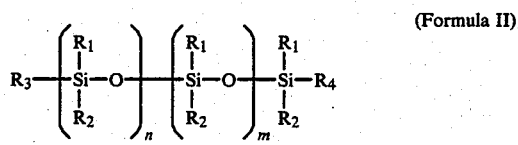

(Formula II)

where $R_1$ and $R_2$ are as given above, preferably methyl, and $R_3$, $R_4$ may be chosen from: aminoalkyl dimethylsilyl, hydroxyalkyl dimethylsilyl, polyethylene oxide dimethylsilyl, carboxyalkyl dimethylsilyl, chloromethyl dimethylsilyl, methacryloxyalkyl dimethylsilyl, and m and n are integers, the sum of which is such that the viscosity is in the range of 50–10,000 cs.

This value is reflective of the presently available compounds.

Finally, the polysiloxane may also be of a tertiary structure as follows:

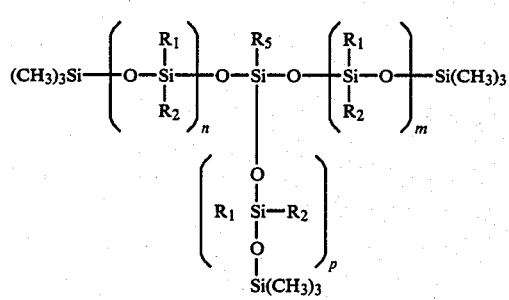

where $R_1$, $R_2$ are as given above, preferably methyl, and $R_5$ may be chosen from: optionally substituted alkyl, optionally substituted aryl, and optionally substituted aralkyl. It should also be noted that tertiary siloxane structures such as this could also be terminated in nonsiloxane moieties; m, n and p are integers the sum of which is sufficient such that the viscosity is in the range of 25–10,000 cs.

Some examples of the modified silicones described above include: Aminopropyldimethyl terminated polydimethylsiloxanes, ethylene-dimethylsiloxane oxide ABA block copolymers (approximately 1–20% polyoxyethylene), dimethylsiloxane-vinylmethyl siloxane copolymers, tertiary structured polydimethylsiloxanes with phenethylsulfonate or carboxypropyl functionalities at the branch points, methyldecylaryloxymethylsiloxane copolymers, polymethyl-3,3,3-trifluoropropylsiloxane, dimethyldiphenylsiloxane copolymers poly(acetoxypropyl)methylsiloxane, polybis(cyanopropyl)siloxane, polydiethoxysiloxane, polydiethylsiloxane, and poly(chlorophenyl)-methylsiloxane.

The preferred polysiloxanes are commercially available polydimethylsiloxanes of viscosities ranging from 50–500 centistokes (cs) which are applied to the casting tape at 0.9 to 9.0 g/m², preferably 1.8 to 5.4 g/m² of casting tape. The higher viscosity fluids up to 350 cs tend to require less material per unit length of tape in order to achieve the desired slippery feel. No significant advantage is apparent in increasing the viscosity from 350 to 500 cs. To these fluids have also been added both ionic and nonionic surfactants. In all cases, casting tape which exhibited reduced tack and dramatically improved moldability resulted with no adverse effect on strength or lamination of the cast.

Ionic and non-ionic surfactants can be added to the silicone fluids in order to further reduce the kinetic coefficient of friction when wet. These include dioctylsulfosuccinate (Aerosol OT), nonionic polyethoxylated room temperature waxy surfactants such as Brij ™, Tergitol ™, Ethosperse ™, Generol ™, and Pluronic ™. In addition, polymeric and clay-type water activated materials have also been added to the silicone fluids to enhance the slippery feel of the casting tape. These materials include polyacrylamides, bentonite, and Keloloid ™ O.

Examples of the polysiloxane embodiments of this invention are shown in Examples 7–14.

B. Surfactants and Polymers Comprised of Hydrophilic Groups

Another aspect of this invention is a modification of the casting tape in orthopedic casts in which the coated rolls of tape are rendered non-tacky after immersion in water by the addition of surfactants or polymers comprised of hydrophilic functional groups to the composition.

As has been suggested, a variety of polymeric materials consisting essentially of hydrophilic groups are suitable for use as lubricants. Examples of such polymers include, but are not limited to water soluble polymers based on ethylenically unsaturated monomers such as acrylamide, vinylpyrrolidone, vinylacetate and its polymeric hydrolyzed derivatives, hydroxy and amino functional lower alkyl acrylates such as 2-hydroxyethyl acrylate and various specialty monomers containing ionic species.

The preferred surfactants and polymers comprised of hydrophilic groups are discussed in Sections 1–3 below.

1. Ionic Alkyl, Aryl or Aralkyl Surfactants

This aspect of the invention relates to the use of paticular lubricants added to polymers used on orthopedic casting tapes which render them non-tacky. In these embodiments, the lubricant consists of ionic alkyl, ionic aryl, or ionic aralkyl compounds. The alkyl compounds generally contain more than about eight contiguous methylene units per molecule which give the compound fatty characteristics. The ionic alkyl compounds can be anionic, cationic or zwitterionic in nature, for example, sodium hexadecyl sulfate and cetyl trimethyl ammonium bromide and lecithin derivatives. Examples of the aryl and aralkyl ionic compounds are the naphthalene sulfonates and alkylbenzene sulfonates, respectively. In practice, the ionic compounds may be added to the isocyanate-functional prepolymer during formulation generally at a level of from about 1.0% to about 5.0% by weight of the total. The curable resin is coated on a sheet in the standard fashion to give rolls of tape. Alternatively, and preferably, the ionic compound can be deposited on the surface of a curable resin coated sheet.

When immersed in water, the tapes quickly become very slippery. The rolls unwind easily and do not stick to gloves. After the roll is wrapped around the limb, molding of the cast becomes easy due to the non-tacky nature of the resin. The cast can be rubbed over its entire length without sticking to the gloves, and the layers of tape do not separate from each other. This pre-lubricating resin approaches the handling characteristics of plaster of Paris bandages very closely.

In summary, the addition of ionic compound surfactants to an isocyanate-functional prepolymer used in orthopedic casting tapes results in a tape which becomes non-tacky after immersion in water. This is advantageous in that the resulting coating material mimics the properties of a plaster bandage in its ease of application and handling. The rolls unwind easily and molding of the cast is facilitated. Despite its slipperiness, the layers of tape laminate well to each other.

2. Polyoxyethylated Surfactants

This aspect of the invention relates to the use of polyoxyethylated surfactants which, when applied to the surface of curable liquid resin coated casting materials or incorporated into the resin, produce a casting product which is slippery and easy to mold to a patient's limb. These materials are of relatively high molecular weight and are generally waxy at room temperature. In addition, the skin permeability and general toxicity of these materials is very low, making them well suited for addition to an orhtopedic bandage. These compounds may be combined with the silicones described above in order to yield a casting material which is non-tacky when dry and very slippery when wet. In addition, these compounds are active as lubricants even when hard water is used to cure the prepolymer.

The following chemical classes of materials when applied to the surface of a casting tape as previously described have been found to yield the desired non-tacky or slippery casting materials.

a. Polyethoxylated Fatty Alcohols

The general structural formula of this class of compounds is represented by the following:

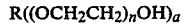  (Formula IV)

wherein
R is a group having a functionality of a and is a saturated or unsaturated alkyl group, optionally halogenated (e.g., chain length $C_8$–$C_{20}$), an aryl group such as an alkylphenyl, or a polyalicylic group (e.g., a sterol derivative);
n is an integer from 3–200, preferably about 20 to about 100; and
a is from 2 to about 10.

The Hydrophile-Lipophile balance (HLB) is greater than 11 and more preferably greater than 15. Examples of these compounds include: Brij TM series, Tergitol TM 15-S series, Generol TM 122E series, Ethosperse TM series, etc. as described below.

It is believed that only those compounds of this class which are solids at room temperature will be effective in producing a slippery casting material with commercially acceptable shelf life for use as an orthopedic bandage.

b. Block Copolymers of Propylene Oxide and Ethylene Oxide

The general structure of this class of compounds may be represented by the following:

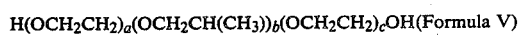

where:
a and c are independently about 3–150, and
b ranges from 0 to about 150 such that the resulting HLB of the compound is greater than about 11.

It has been found that a high molecular weight polyethylene oxide (available from Union Carbide as Carbowax TM) applied to the surface does yield a non-tacky casting material, however, the material was not as slippery as that of the polymeric materials described in 2 a. and b. above of similar molecular weight.

Many surfactants, detergents, and emulsifiers may be useful as slip agents but are unsuitable for use with an isocyanate-functional prepolymer because they adversely affect the shelf-life of that prepolymer and, more importantly for medical uses, as deleterious to skin. Non-ionic surfactants, especially those of higher molecular weight described herein, are known to have extremely low or nondetectable skin permeability and are often reported as additives to cosmetic and pharmaceutical formulations as a means of reducing skin permeability to detergents and other more toxic substances. The nonionic surfactants of this invention, for the most part, are not skin irritants and usually contain functionalities which allow them to react with the resin, thus minimizing the possibility of direct or prolonged skin contact.

The surfactants useful in this invention are commercially available from many suppliers. The following have been shown to be useful:
ICI Americas Inc.:
Brij TM 58—20 mole polyoxyethylene cetyl ether,
Brij TM 78—20 mole polyoxyethylene stearyl ether,
Brij TM 99—20 mole polyoxyethylene oleyl ether,
Brij TM 700—100 mole polyoxyethylene stearyl ether;
Glyco Chemicals Inc. (Williamsport Pa.):
Ethosperse TM CA-20—20 mole polyoxyethylene stearyl ether,
Pegosperse TM CO-200—200 mole polyoxyethylene castor oil;
Henkel-Speciality Chemicals Div. Teaneck, N.J.:

Generol TM 122E-16—16 mole polyethylene glycol soya sterol,
Generol TM 122E-25—25 mole polyethylene glycol soya sterol,
Eumulgin TM B2—fatty alcohol polyglycol ether; Union Carbide:
Tergitol TM 15-S-40—Alkoxy ($C_{12}$–$C_{14}$) polyethyleneoxyethanol avg. molecular weight (M.W.) 1960,
Tergitol TM NP-40—Nonylphenol polyethylene glycol ether avg. molecular weight 1980;
BASF Wyandote:
Pluronic TM F-68 Polyethylene oxide terminated polypropylene oxide, 80 mole % EO, avg. M.W.=8350,
Pluronic TM F108 Polyethylene oxide terminated polypropylene oxide, 80 mole % EO, avg. M.W.=14,500,
Pluronic TM F127 Polyethylene oxide terminated polypropylene oxide, 70 mole % EO, avg. M.W.=12,500,
Pluronic TM P65 Polyethylene oxide terminated polypropylene oxide, 50 mole % EO, avg. M.W.=3400.
Other suppliers are available for these types of surfactants. In order to achieve a non-tacky feel both dry and wet, these surfactants are usually combined with the silicone fluids described above.

3. Ionic Derivatives of Polyethoxylated Alcohols

This aspect of the invention relates to the use of ionic derivatives of polyethoxylated alcohols (IPEA) which when applied to the surface of isocyanate-functional prepolymer casting resins effectively reduce or eliminate the tack without significantly affecting other properties of the casting material. This effectively increases the ease of application of the casting tape as well as the moldability to the patient's limb. The IPEA class of materials is useful in synthetic casting resins for several reasons: IPEA's have very low or no skin permeability and in most cases no skin irritation; many yield little or no foaming; IPEA's are active in hard water (e.g., in water used for plaster casts); and in most cases, the IPEA surfactants are waxy, and therefore, can be applied to the surface of the casting tape in a molten state and subsequently allowed to solidify. This latter property allows the surfactant to remain on the surface of the type where it is most active and also makes the roll easier to unwind.

Specifically, the following surfactant structures will yield the desired properties:

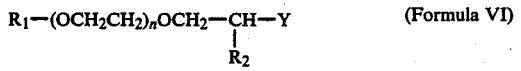

(Formula VI)

where
$R_1$ may be a straight or branched chain hydrocarbon and n is at least 3. The length of the hydrocarbon must be in balance with that of the polyethylene oxide to give the ethoxylated nonionic primary alcohol a HLB in the range of 11–35 and more preferably in the range of 15–25. $R_1$ may be selected from saturated or unsaturated optionally halogenated alkyl (preferably $C_1$–$C_{20}$, more preferably $C_8$–$C_{18}$), aryl or optionally substituted aryl, and aralkyl (preferably $C_7$–$C_{24}$).
Y is a derivative of the alcohol and is an organic or inorganic salt of a group selected from $-OSO_3H$, $-SO_3H$, $-OPO_3H$, $-PO_3H$, and $-N(R_1)_3^+$.
$R_2$ is hydrogen or is selected from the same group as $R_1$.

It has been found that the IPEA's described herein can either be added directly to the resin at concentrations ranging from 0.5–7% or preferably, applied to the surface of the tape at coating weights of 0.45 to 6.3 g/m² (preferably 0.9 to 3.6 g/m²). The higher melting compounds may be suspended in a carrier fluid such as silicones, organic oils, or suitable solvents in order to be sprayed. Silicone fluids or nonionic polyethoxylated waxes, such as those described above, may be used in conjunction with the IPEA in order to augment the slippery feel. Furthermore, it is possible that other surfactants which may be more skin irritating than some of those of the IPEA may be added in reduced amounts in order to increase the slipperiness of the casting material without compromising the skin biocompatibility. In addition, bactericidal surfactants may also be added in order to effectively kill bacteria between the skin and cast for better hygiene (e.g., benzalkonium chloride or Cetrimide B.P.).

IPEA type surfactants are commercially available from several chemical suppliers including Shell Chemical (Neodol TM 3S and 3A), Henkel TM (Standopol series), and DuPont Zonyl TM UR (polyfluoroaliphatic ethoxylated phosphonate).

III. COMBINED LUBRICANTS

As noted above, the lubricant may be comprised of both hydrophilic groups bound to the prepolymer and one or more additive lubricants. The particular procedures used in obtaining a bound lubricant and the particular procedures used with additive lubricants are used in conjunction with one another, generally without modification. For example, a casting tape coated with a curable liquid resin having bound hydrophilic groups in accordance with Example 1 below can be coated with a polysiloxane lubricant in accordance with Examples 6–13, to obtain an article in accordance with this invention, as in Example 23.

One advantage of the combined lubricants resides in the pre-wetted reduction in tack provided by a polysiloxane and the great reduction in tack provided by a bound lubricant after initiation of cure by exposure to water.

EXAMPLES

Test for Determining the Coefficient of Friction of Synthetic Casting Tapes

Determination of the frictional properties of many materials is often measured in terms of the coefficient of friction. This type of measurement may be made when sliding the material of interest over itself or over another object. The coefficient of friction is a dimensionless term which quantifies the frictional properties and may distinguish between surfaces of varying roughness, tackiness, slipperiness, etc. In the present application, a wide variety of lubricating properties are generated by surfactants or other surface active materials which are either added directly to the casting resins prior to coating the scrim, or applied to precoated tape. A test has been developed which measures the tack, i.e., kinetic coefficient of friction of these various materials. This test method is based on ASTM test method D 1894 ("Static and Kinetic Coefficients of Friction of Plastic Film and Sheeting") and measured the kinetic coefficient of friction between a horizontal stationary piece of test specimen in low tension and a 200 g 304 stainless steel sled polished to a No. 4 finish. The procedure and apparatus of ASTM test method D 1894 have been modified to accommodate relatively rough and elastic materials such as synthetic casting tapes. This method yields empirical data which, for the most part, correlates with actual performance and thereby offers a quantitative measurement of the lubricating properties of a given casting material.

As used herein, the following terms have the following meanings:

"Kinetic Friction"—the resisting or opposing force that arises when a source of one object slides over the surface of another object. "Kinetic Coefficient of Friction"—(KCOF) the ratio of the kinetic frictional force to the force acting perpendicularly to the two surfaces in contact (usually the gravitational force). This dimensionless term is a measure of the relative difficulty with which the two materials will slide across one another i.e., the higher the coefficient of friction, the more difficult it is to slide the two materials over one another. The kinetic coefficient of friction, as used herein, is determined from the test described hereinafter and is calculated by the equation:

$$\text{Kinetic Coefficient of Friction} = \frac{\text{force required to pull the sled(g)}}{200 \text{ (g)}}$$

Test Method

SAMPLE AND MATERIALS CONDITIONING

Sample Conditioning—Test samples should be conditioned at 21°-25° C. for not less than 24 hours prior to testing.

Water Conditioning—Water for use in this test should be deionized or soft water conditioned to 22°-24° C. Fresh water should be used for each set of samples, i.e., for each lot of test samples.

Test Conditions—Testing must be conducted in a controlled temperature and humidity environment of 21°-25° C. and 45-55% relative humidity.

APPARATUS

A. Sled—A 304 stainless steel half round cylinder 4.92 cm (1 15/16") diameter by 2.54 cm (1.000") wide and 2.54 cm (1.000") high with a 4-40 0.5" thread in one end into which an Instron part no. T53-5 eye screw is fastened. Material is added or removed from the top of the sled so as to adjust the weight to 200±0.5 g. The radiused face of the sled is polished to a No. 4 finish.

B. Test Fixture—The Instron Coefficient of Friction Fixture (Catalog No. 2810-005) was modified to accommodate testing of casting materials. Specifically, the pulley assembly was raised 2.54 cm (1.000") and an additional Teflon TM coated brass tension pulley 0.953 cm (0.375") in diameter × 13.34 cm (5.25") was fixed to the end of the table opposite the load pulley and positioned such that the top of the pulley was in the plane of the table. In addition, a 12.7 cm (5")×0.953 cm (0.375")×0.953 cm (0.0375") hold down clamp was positioned 7.62 cm (3.0") from the load pulley in order to fix the test specimen in place. A series of weights fixed to spring clamps were fabricated in order to keep the test specimen in tension. The proper weight is determined by the width of the test sample, 0.045 kg/cm (¼ lb/inch) (e.g., with a 7.62 cm (3") wide test specimen a 1.65 kg (¼ lb) weight should be used).

C. Force Measuring Device—An Instron Model No. 1122 Table top measuring instrument equipped with a 50 lb. load cell (Instron assembly No. A-30-39) and connected to an Instron Microcon II microprocessor Model No. MC4100.

PREPARATION OF APPARATUS

1. Assemble the apparatus as described above.
2. Set the drive speed of the sled (i.e., the crosshead speed) to 127 cm (50 inches)/min.
3. Calibrate the 50 lb. load cell using a 500 g weight.
4. The following settings on the control panel of the Instron Model No. 1122 measuring device should be set:
   crosshead speed=127 cm (50 in)/min
   full scale load=0-500 g
   chart speed=12.7 cm (5 in)/min auto
   load cell filter=in
   polarity=up The Microcon II microprocessor should be set to the following:
area=0
gage length=2.54 cm (1.0 inch)
speed=127 cm (50 in)/min
fail criteria=100%
load limit=45,360 K grams force
elongation=100%
crosshead stop=off
elongation correction factor=no correction 5. Set up the Microcon II microprocessor Model No. MC4100 to integrate the tension force for travel between 1.27 cm and 19.0 cm (0.5 and 7.5 inches) and to calculate the average tension force. Be sure the first 1.27 cm (0.5") of travel is not included in this calculation to avoid incorporating the static functional force.

PROCEDURE

The following procedure is approriate for water-activated casting materials which set, i.e., resist passive motion in about three to five minutes. The water immersion time and subsequent waiting time to initiation of sled movement may require adjustment if the set time of the material to be tested is substantially different from three to five minutes. This procedure is also used to determine the coefficient of friction of dry material by eliminating the water immersion and subsequent waiting time.

1. Open the pouch containing the test specimen, immediately cut the sample to obtain a length of from 46 cm to 61 cm (18 in. to 24 in.) and immediately immerse the sample into 3.8 liter (1 gallon) of fresh 22°-24° C. tap water without agitation of any kind. Start a stopwatch immediately upon immersion in the water.
2. After 15 seconds gently remove the test specimen (avoid any agitation) from the water and briskly shake the specimen twice to remove excess water.
3. While avoiding contact with the specimen as much as possible, place the sample flat on the testing table and fix one end into the hold down clamp and attach the proper weight (0.045 kg/cm width or ¼ lb/inch width of tape) to the free end.
4. 15 seconds after the specimen has been removed from the water, gently place the sled on the specimen such that the wire is straight without sagging and under 10-15 g tension.
5. Exactly 3 seconds after the sled has been placed on the specimen, start the driving mechanism which was previously adjusted to a crosshead speed of 127 cm (50 inches)/min.
6. Record the average tension force calculated by the Microcon II microprocessor.

7. Remove the sled and immediately clean the polished sliding surface with a soft paper towel and a solution of 50% acetone and 50% ethanol. Allow the sled to dry.

8. Remove the test specimen, dry and clean off the table, tension pulley, and clamp. If necessary use the cleaning solution of step 7.

EXAMPLES 1-6

Bound Lubricants

EXAMPLE 1

A 3.8 liter (one gallon) glass vessel equipped with a 12.7 cm×2.54 cm×0.318 cm (5×1×⅛") Teflon ™ impeller, addition funnel, nitrogen purge line, and thermometer was assembled and purged with nitrogen for 30 minutes to ensure the entire apparatus was completely dry. The following chemicals were added to the reactor through the addition funnel in order and at 5 minute intervals:

| Chemical | Wt (g) | Wt. % |
|---|---|---|
| Isonate 143L (Upjohn Co.) | 2151.7 | 58.15 |
| Benzoyl Chloride | 2.59 | 0.07 |
| Pluronic F-108 (BASF) | 148.0 | 4.00 |
| DB-100 (Dow Chemical) | 6.66 | 0.18 |
| butylated hydroxy toluene (BHT) | 17.76 | 0.48 |
| PPG-425 (Union Carbide) | 217.45 | 5.88 |
| PPG-725 (Union Carbide) | 1109.56 | 29.99 |
| MEMPE | 46.25 | 1.25 |

The agitation rate was gradually increased as the viscosity increased. The vessel was temporarily insulated with glass wool and the temperature of the reaction was allowed to increase (due to reaction exotherm) to 55° C. The glass wool was removed along with the agitator, thermometer, and addition funnel. The vessel was sealed and the resin was allowed to cool for 24 hours.

The resin was coated onto three inch wide knit fiberglass scrim as described in U.S. Ser. No. 668,881, filed Nov. 6, 1984, at a resin content of 42.5% by weight. The coated fabric was converted to individual rolls 3.66 m (12 feet) in length. These rolls were packaged individually into moisure proof pouches. Ten days after cooling, two of the rolls were unpackaged in a 2% relative humidity environment and cut to 61 cm (24 inch) lengths and resealed individually in the moisture-proof pouches.

Each 60.96 cm (24") sample was then tested according to the KCOF method described above. The samples were found to have a mean kinetic coefficient of friction of 0.29.

EXAMPLE 2

The following resin was prepared, coated and packaged according to the procedure of Example 1:

| Chemical | Wt (g) | Wt % |
|---|---|---|
| Isonate ™ 143 L (Upjohn Co.) | 2183 | 59.0 |
| Benzoyl Chloride | 2.6 | .07 |
| Brij ™ 700 (ICI Americas Inc.) | 148.0 | 4.0 |
| DB-100 (Dow Chemical) | 6.7 | .18 |
| BHT | 17.8 | .48 |
| PPG-425 (Union Carbide) | 270.1 | 7.3 |
| PPG-725 (Union Carbide) | 1016.4 | 27.5 |

-continued

| Chemical | Wt (g) | Wt % |
|---|---|---|
| MEMPE | 55.5 | 1.5 |

Note:
Brij 700 is a polyoxyethylene (avg. mol. wt. 100) stearyl ether

This material was tested according to the KCOF method and exhibited a mean kinetic coefficient of friction of 0.28.

EXAMPLE 3

The following resin was prepared, coated and packaged according to the procedure of Example 1:

| Chemical | Wt (g) | Wt % |
|---|---|---|
| Isonate 143L | 2045 | 58.4 |
| Benzoyl Chloride | 2.5 | .07 |
| PEG 8000 | 157.5 | 4.5 |
| DB-100 | 6.3 | .18 |
| BHT | 16.8 | .48 |
| PPG-425 | 280.9 | 8.0 |
| PPG-725 | 947.1 | 27.1 |
| MEMPE | 43.75 | 1.25 |

Note:
PEG-8000 is a polyethylene glycol, having a molecular weight of approx. 8000.

This method was tested according to the KCOF method and exhibited a mean kinetic coefficient of friction of 0.27.

EXAMPLE 4

A hydrophilic oligomeric diol was prepared by reacting dried polyethylene oxide glycol (available from Union Carbide as Carbowax ® 1000) with dried dimethyl sodium sulfoisophthalate in a 4:1 molar ratio at about 220°–250° C. in the presence of a catalytic amount of zinc acetate. This diol, in an amount of 15,164 g, was combined with 1920 grams of trimethylol propane and the mixture was dried by azeotroping with toluene. This was then charged directly into a nitrogen purged vessel containing 26,559 grams of Isonate 143L, 218 g of BHT and 25 g of ethanesulfonic acid. After mixing for about 2 hours at about 60°–80° C., the product was transferred to several 3.785 liter (one gallon) glass jars and sealed under a nitrogen blanket.

One jar containing 4222 grams of the above sulfonated urethane resin was heated at 65° C. (150° F.) for about two hours and then 42 grams of 2,2'-dimorpholinodiethyl ether were mixed in. In a dry room with the humidity held at about 2% relative humidity, the resin was then coated onto three inch wide knit fiberglass scrim as previously described at a resin content of 39.9% by weight. The coated scrim was converted to twelve foot lengths by rerolling onto polyethylene cores and cutting to length. These rolls were packaged individually in moisture-proof pouches.

Five months after coating, the samples were tested according to the KCOF method. These samples were found to have a mean kinetic coefficient of friction of 0.46.

EXAMPLE 5

About one month after coating the scrim in Example 4, several rolls of this material were sprayed on both sides with polydimethylsiloxane 200-100 cs (Dow Corning) at a coating weight of 3.4 g/m² in a dry room with the relative humidity held at about 2%. Each length of material was rerolled and sealed in a moisture-proof pouch.

After about 4 months, several samples were tested according to the KCOF method and were found to have an average kinetic coefficient of friction of 0.40. In addition, one sample was tested dry according to the KCOF method, i.e., it was not immersed in water. This sample was found to have a mean kinetic coefficient of friction of 0.32.

EXAMPLE 6

A hydrophilic, oligomeric diol, was prepared by reacting dried polyethylene oxide glycol (Carbowax ® 600) with dried dimethyl sodium sulfoisophthalate in a 2:1 molar ratio, at 220°–250° C., in the presence of a catalytic amount of zinc acetate. This diol, in the amount of 71.0 grams (0.11 eq.) was combined wiht 128.0 grams (0.59 eq.) PPG-425 and 49.0 grams (0.10 eq.) PPG-1025. To the stirred mixture, under a nitrogen sweep, were added 3.1 grams BHT, 0.46 grams benzoyl chloride, 13.3 grams 2,2'-dimorpholinodiethyl ether and 403.0 grams (2.80 eq.) Isonate 143L. The reaction mixture was allowed to exotherm and stirring was continued for 2 hours while the resin cooled.

The resin was coated and packaged according to the procedure of Example 1 except that the resin content was 42% by weight. Samples were tested according to the KCOF method and exhibited a mean coefficient of friction of 0.31.

EXAMPLES 7–14

Polysiloxane Lubricants

In the following Examples, the fluid was sprayed on 7.6 cm (3") casting tape available from 3M as SCOTCHCAST ™ 2 comprising a knit fiberglass scrim impregnated with an isocyanate-functional prepolymer resin. Spraying was accomplished using either a modified air-brush or a Spraying Systems, Wheaton, IL., atomizing ¼ J Spray nozzle unless otherwise indicated. Both sides of the tape were sprayed. The amount of fluid per unit length of tape was controlled by the speed at which the tape was drawn past the sprayer was well as by regulating the flow rate of the spraying apparatus.

EXAMPLE 7

Dow corning 200-300 cs silicone fluid was sprayed on both surfaces of a casting tape as previously described at a total coating weight of 3.95 g/m$^2$. The resulting casting material was very easy to handle both before and after wetting. The sample was then tested according to the KCOF method. The samples exhibited a mean kinetic coefficient of friction of 0.52.

EXAMPLE 8

Dow Corning 200-500 cs silicone fluid was sprayed on both sides of a casting tape as previously described at a coating weight of 3.2 g/m$^2$. The mean kinetic COF was 0.62.

EXAMPLE 9

Dow Corning 200-100 cs silicone fluid containing 5% wt/wt Aresol OT (dioctylsulfosuccinate sodium salt) was sprayed on both sides of a casting tape as previously described at a coating weight of 3.2 g/m$^2$. The mean kinetic COF was 0.45.

EXAMPLE 10

Dow Corning 200-50 cs silicone fluid containing 12.3% wt/wt Keloloid O was sprayed on both sides of a casting tape as previously described at a coating weight of 4.3 g/m$^2$ roll. The mean kinetic COF was 0.52.

EXAMPLE 11

A tertiary structure polydimethylsiloxane with carboxypropyl groups at the branch points (avail. from Petrarch Systems Inc. as PS-402) was sprayed onto both sides of a casting tape as previously described at a total coating weight of 3.6 g/sq. meter. This material was tested for its lubricating properties according to the procedure of KCOF method and was found to have a mean kinetic coefficient of friction of 0.49.

EXAMPLE 12

A (95–98%) methyldecyl (2–5%) aryloxymethylsiloxane copolymer available from Petrarch Systems Inc. as PS136 was sprayed onto both surfaces of casting tape as previously described at a total coating weight of 3.41 g/sq. meter. This material was tested for its lubricating properties according to the KCOF method and was found to have a mean kinetic coefficient of friction of 0.49.

EXAMPLE 13

A polydimethyl 3,3,3 trifluoropropylsiloxane available from Petrarch Systems as PS181 was sprayed onto both sides of casting tape as previously described at a total coating weight of 2.33 g/sq. meter. This material was tested for its lubricating properties according to the KCOF method and was found to have a mean kinetic coefficient of friction of 0.69.

EXAMPLE 14

A (83–85%) dimethyl (15–17%) diphenylsiloxane vinyl terminated copolymer available from petrarch Systems, Inc. as PS782 was sprayed onto both sides of casting tape as previously described at a total coating weight of 3.2 g/sq. meter. This material was tested for its lubricating properties according to the KCOF method and was found to have a mean kinetic coefficient of friction of 0.55.

EXAMPLES 15 AND 16

Polymers Comprised of Hydrophilic Groups

EXAMPLE 15

Cyanomer ™ A370 (a polyacrylamide available from American Cyanamide) was coated onto a casting tape, available from 3M as Scotchcast 2 as in Examples 7–14, using a vibratory screen at a coating weight of 4.8 g/m$^2$. The resulting casting tape was tested according to the KCOF method and found to have a mean kinetic coefficient of friction of 0.32.

EXAMPLE 16

A 115,000 molecular weight poylvinyl alcohol available from Aldrich Chemicals, (P.N. 18251-6) was coated onto casting tape as previously described in Examples 7–14, according to the procedure of Example 15, at a coating weight of 4.2 g/m$^2$. The resulting casting tape was tested according to the KCOF method and found to have a mean kinetic coefficient of friction of 0.42.

EXAMPLES 17-27

Surfactant Lubricants

In the following examples the surfactant(s) or surfactant/silicone fluid combination was sprayed, except as noted, on the surface of a casting tape, which tape was previously described in Examples 7-14. An air brush was used to spray on the material. In most cases it was necessary to spray on the material in a hot molten sate in which case the material solidified almost instantaneously upon expansion and exit from the nozzle. Both sides of the casting material were coated with equivalent amounts.

EXAMPLE 17

Casting tape as previously described in Examples 7-14 was evenly coated with Metarin TM P (a 95% phosphatides lecithin composition available from Lucas Meyer Inc., Decatur, Ill.) at a coating weight of 3.6 g/m². The Metarin P was deposited on the casting tape using a vibratory screen. This resulting casting tape was tested according to the KCOF method and found to have a mean kinetic coefficient of friction of 0.19.

EXAMPLE 18

Sodium dodecyl sulfate was coated onto a casting tape as previously described in Examples 7-14 according to the procedure of Example 15 at a coating weight of 3.6 g/m². The resulting casting tape was tested according to the KCOF method and found to have a mean kinetic coefficient of friction of 0.23.

EXAMPLE 19

The following resin was prepared, coated and packaged according to the procedure of Example 1 except that the Standopol TM 125E (available from Henkel Corp.) was first dried to remove water.

| Chemical | Wt. (g) | Wt. % |
| --- | --- | --- |
| Isonate TM 143L | 1435.5 | 52.5 |
| Benzoyl Chloride | 1.9 | .07 |
| DMDEE (Texaco) | 77.38 | 2.83 |
| DB-100 | 5.0 | .18 |
| BHT | 12.72 | 0.47 |
| PPG-725 | 1117.5 | 40.9 |
| Standopol TM 125E* | 82.0 | 3.0 |

Standpol TM 125E is the sodium sulfonate of a 12 mole ethylene oxide lauryl ether available from Henkel Corp.)

This material was tested according to the KCOF method and exhibited a mean kinetic COF of 0.35.

EXAMPLE 20

Generol TM 122E-25 was sprayed on both surfaces of a casting tape at a coating weight of 3.2-3.6 g/m². The resulting casting material was very slippery when wet. The mean kinetic COF was 0.25.

EXAMPLE 21

Tergitol TM 15-S-40 dispersed in Dow Corning 200-100 cs silicone oil (1:1 w/w) was sprayed on both surfaces of a casting tape at a coating weight of 3.6 g/m². The product was both non-tacky dry and very slippery when wet. The mean kinetic COF was 0.31.

EXAMPLE 22

Tergitol TM NP-40 was sprayed on both surfaces of a casting tape as previously described in Examples 7-14 at a coating weight of 3.6 g/m². The mean kinetic COF was 0.27.

EXAMPLE 23

Brij 58 TM and Brij TM 78 were sprayed on both surfaces of separate rolls of a casting tape as previously described in Examples 7-14 at coating weights of 3.6 and 3.8 g/m². The mean kinetic COF of each was 0.32 and 0.37, respectively.

EXAMPLE 24

Ethosphere TM CA20 was sprayed on both surfaces of a casting tape as previously described in Examples 7-14 at a total coating weight of 3.2-2.6 g/sq. meter. The mean kinetic COF was determined to be 0.26.

EXAMPLE 25

Anhydrous Neodol TM 3A (ammonium salt of a 3 mol ethoxylated laureth sulfate) was added in a molten state to hot Dow silicone 200-100 cs fluid to 50% wt/wt and, the resulting mixture was sprayed on both surfaces of a casting tape as previously described in Examples 7-14 at coating weight of 3.6 g/m². The mean kinetic COF was 0.43.

EXAMPLE 26

Anhydrous Standopol TM 125E (sodium salt of a 12 mole ethoxylated laureth sulfate) was also added in a molten state to hot Dow silicone 200-100 cs fluid to 50% wt/wt, and the resulting mixture was sprayed on both sides of a casting tape as previously described in Examples 7-14 at coating weight of 2.7-3.2 g/m². The mean kinetic COF was 0.38.

EXAMPLE 27

The following resin formulation was prepared and converted according to the procedure of Example 1. The slip additive, Zonyl TM UR available from E.I. duPont de Nemours & Co. Wilmington, Del., is a mixture of polyfluoroaliphatic ethoxylated phosphonates having the general structure $((FCH_2CH_2)_{3.8}(OCH_2CH_2)_{1,2}OP(OH)_{2,1})$.

| Chemical | Wt. g | Wt. % |
| --- | --- | --- |
| Isonate TM 143L (Upjohn) | 1083.3 | 50.8 |
| Benzoyl Chloride | 1.4 | .07 |
| Dimorpholinodiethyl ether (DMDEE) | 58.4 | 2.74 |
| DB-100 (Dow Chemical) | 3.6 | .17 |
| BHT | 9.6 | .45 |
| PPG-725 (Union Carbide) | 843.3 | 39.5 |
| Zonyl TM UR (DuPont) | 134.4 | 6.3 |

The resulting casting material was tested according to the KCOF method and found to have a mean kinetic COF of 0.93.

Combination Lubricants

EXAMPLE 28

The casting material was produced according to the procedure of Example 1 except that during the converting operation the coated scrim was sprayed with Dow polydimethylsiloxane 200-100 cs. The spraying was done using an air atomizing nozzle at approximately 2.65 g/m² applied to each side of the casting tape. When tested according to the KCOF method, the samples were found to have a mean kinetic coefficient of friction of 0.33.

COMPARATIVE EXAMPLES A AND B

The following resin was prepared, coated and packaged according to the procedure of Example 1:

| Chemical | Wt (g) | Wt % |
|---|---|---|
| Isonate TM 143L (Upjohn Co.) | 2046.10 | 55.30 |
| Benzoyl Chloride | 3.68 | .10 |
| PPG-725 (Union Carbide) | 1582.85 | 43.05 |
| Dimethyl Ethanolamine | 9.28 | .25 |
| Niax TM A-99 (Union Carbide) | 11.14 | .30 |
| LK-221 (Air Products) | 36.94 | 1.00 |

This material was tested according to the KCOF method and exhibited a mean kinetic COF of 2.06.

The following resin was prepared, coated and packaged according to the procedure of Example 1:

| Chemical | Wt (g) | Wt % |
|---|---|---|
| Isonate TM 143L (Upjohn Co.) | 2046.10 | 55.30 |
| Benzoyl Chloride | 3.70 | .10 |
| DB-100 (Dow Chemical) | 37.00 | 1.00 |
| PPG-725 (Union Carbide) | 1592.85 | 43.05 |
| Dimethylethanolamine | 9.25 | .25 |
| Niax TM A-99 (Union Carbide) | 11.10 | .30 |

This material was tested according to the KCOF method and exhibited a mean kinetic COF of 1.76.

It has been found that the tack of a given isocyanate-functional prepolymer tends to peak during cure. Accordingly, prepolymers which have a longer set time than those exemplified herein, may not exhibit a kinetic COF as high as those of Comparative Examples A and B because cure has not progressed sufficiently at the time specified in the foregoing test procedure. Therefore, the relative rate of cure of prepolymers tested according to the foregoing method should be considered when comparing results of the test for prepolymer systems having variable rates of cure.

EXAMPLE 29

The following example illustrates the average and synergism between the use of both a topical silicone treatment and a lubricating agent (Pluronic F108) added to the resin system.

The following resin was prepared and converted according to the procedure of Example 1.

| Chemical | wt. g | wt (%) |
|---|---|---|
| Isonate TM 143L | 2162.6 | 58.5 |
| Benzoyl Chloride | 2.6 | .07 |
| Pluronic F108 | 148.1 | 4.0 |
| DB-100 | 6.7 | 0.18 |
| BHT | 17.8 | .48 |
| PPG-425 | 270.2 | 7.3 |
| PPG-725 | 1045.9 | 28.3 |
| MEMPE | 46.3 | 1.25 |

The resulting coating material was tested according to the KCOF method with the omission of the water dip (Procedure step 2), i.e., the casting material was tested in a "dry" state. The mean kinetic coefficient of friction was determined to be 2.18.

A casting material prepared according to the procedure above was sprayed with Dow 200-100 centistoke silicone fluid according to the procedure of Example 28. The resulting orthopedic bandage was tested for its lubricating properties in a "dry" state according to the procedure of Example A. The mean kinetic coefficient of friction was found to be 0.80.

The mean kinetic coefficient of friction of the silicone sprayed material wetted in accordance with the KCOF method was 0.33.

What is claimed is:

1. An article comprising adjacent layers of a pre-lubricated, curable resin-coated sheet wherein an exposed major surface of the sheet exhibits a kinetic coefficient of friction of less than about 1.2 and wherein the resin in not appreciably dispersible in water and the adjacent layers are laminatable after immersion in water.

2. An orthopedic support material comprising a curable resin-coated sheet having a lubricant at an exposed major surface of the resin-coated sheet, wherein said lubricant is comprised of:
   (a) hydrophilic groups which are covalently bonded to the curable resin, or
   (b) an additive which forms a layer on the surface of the curable resin, or
   (c) a combination of (a) and (b);

and wherein during curing said lubricant is present in an amount such that the kinetic coefficient of friction of the exposed major surface of the resin-coated sheet is less than about 1.2, and wherein said resin is not appreciably dispersible in water and adjacent layers of said resin-coated sheet are laminatable after immersion in water.

3. An orthopedic article comprising a sheet impregnated with a pre-lubricated, curable and crosslinkable resin, wherein an exposed major surface of said resin-impregnated sheet exhibits a kinetic coefficient of friction of less than about 1.2, and wherein said resin is not appreciably dispersible in water and adjacent layers of said resin-impregnated sheet are laminatable after immersion in water.

4. An orthopedic article in accordance with claim 3 wherein said pre-lubricated resin comprises a lubricant at the exposed major surface of the resin-impregnated sheet, said lubricant comprising:
   (a) hydrophilic groups which are covalently bonded to the curable resin, or
   (b) an additive which is incompatible with the curable resin, or
   (c) a combination of (a) and (b);

and wherein said lubricant is present in an amount such that the kinetic coefficient of friction of the exposed major surface of the resin-impregnated sheet is less than about 1.2.

5. An orthopedic article in accordance with claim 4 wherein said lubricant comprises hydrophilic groups which are covalently bound to the curable resin, said hydrophilic groups comprising polyethylene oxide groups.

6. An orthopedic article in accordance with claim 5 wherein said polyethylene oxide comprises less than about 15% by weight of said resin.

7. An orthopedic article in accordance with claim 5 wherein said polyethylene oxide comprises less than about 10% by weight of said resin.

8. An orthopedic article in accordance with claim 5 wherein said polyethylene oxide comprises less than about 6% by weight of said resin.

9. An orthopedic article in accordance with claim 5 wherein said polyethylene oxide comprises about 3% to 4% by weight of said resin.

10. An orthopedic article in accordance with claim 4 wherein the curable resin is water-curable.

11. An orthopedic article in accordance with claim 10 wherein the water-curable resin is an isocyanate-functional prepolymer.

12. An orthopedic article in accordance with claim 10 wherein the water-curable resin comprises a polyurethane prepolymer.

13. An orthopedic article in accordance with claim 10 wherein the water-curable resin comprises a cyanoacrylate ester.

14. An orthopedic article in accordance with claim 10 wherein the water-curable resin comprises an epoxy resin.

15. An orthopedic article in accordance with claim 10 wherein the water-curable resin comprises a prepolymer terminated at its ends with trialkoxy-silane or trihalo-silane groups.

16. An orthopedic article in accordance with claim 3 wherein said pre-lubricated resin comprises an additive selected from the group consisting of:
(i) a surfactant,
(ii) a polymer comprised of a plurality of hydrophilic groups,
(iii) a polysiloxane, and
(iv) mixtures of any of (i), (ii), and (iii).

17. An orthopedic article in accordance with claim 16 wherein the additive comprises a polymer having a plurality of hydrophilic groups.

18. An orthopedic article in accordance with claim 17 wherein said polymer additive comprises polyethylene oxide groups.

19. An orthopedic article in accordance with claim 18 wherein said polyethylene oxide comprises less than about 15% by weight of said resin.

20. An orthopedic article in accordance with claim 18 wherein said polyethylene oxide comprises less than about 10% by weight of said resin.

21. An orthopedic article in accordance with claim 18 wherein said polyethylene oxide comprises less than about 6% by weight of said resin.

22. An orthopedic article in accordance with claim 18 wherein said polyethylene oxide comprises about 3% to 4% by weight of said resin.

23. An orthopedic article in accordance with claim 16 wherein the additive comprises a polysiloxane.

24. An orthopedic article in accordance with claim 23 wherein said polysiloxane additive is deposited as a layer on said exposed major surface of said resin-impregnated sheet in an amount sufficient to impart a kinetic coefficient of friction of less than about 1.2 to said exposed major surface.

25. An orthopedic article in accordance with claim 24 wherein said polysiloxane layer is deposited on said exposed major surface in an amount of from about 0.9 g/m$^2$ to about 9 g/m$^2$.

26. An orthopedic article in accordance with claim 24 wherein said polysiloxane layer is deposited on said exposed major surface in an amount of from about 1.8 g/m$^2$ to about 5.4 g/m$^2$.

27. An orthopedic article in accordance with claim 23 wherein the polysiloxane has a viscosity of at least about 50 cs.

28. An orthopedic article in accordance with claim 16 wherein the additive comprises a polydimethylsiloxane.

29. An orthopedic article in accordance with claim 16 wherein the additive comprises a surfactant.

30. An orthopedic article in accordance with claim 29 wherein the surfactant is an alkyl, aryl, or aralkyl ionic compound.

31. An orthopedic article in accordance with claim 29 wherein the surfactant is a polyethoxylated surfactant.

32. An orthopedic article in accordance with claim 31 wherein the polyethoxylated surfactant additive is nonionic.

33. An orthopedic article in accordance with claim 32 wherein the polyethoxylated surfactant additive is a solid at ambient temperatures.

34. An orthopedic article in accordance with claim 3 wherein the sheet comprises a fiberglass fabric.

35. An orthopedic article in accordance with claim 34 wherein the fiberglass fabric is an extensible, heat set, knit fiberglass fabric.

36. An orthopedic article in accordance with claim 34 wherein the curable resin comprises a water-curable, isocyanate-functional prepolymer which is a derivative of an aromatic polyisocyanate.

37. An orthopedic article in accordance with claim 3 wherein the sheet comprises a nonnwoven fabric.

38. An orthopedic article in accordance with claim 3 wherein the sheet comprises a woven fabric.

39. An orthopedic article in accordance with claim 3 wherein the sheet comprises a knit fabric.

40. An orthopedic article in accordance with claim 3 wherein the resin is cured.

41. An orthopedic article in accordance with claim 3 wherein after immersion in water at least about 70% of said resin is retained in said resin-impregnated sheet.

42. An orthopedic article in accordance with claim 3 wherein after immersion in water at least about 85% of said resin is retained in said resin-impregnated sheet.

43. An orthopedic article in accordance with claim 3 wherein after immersion in water at least about 95% of said resin is retained in said resin-impregnated sheet.

44. An orthopedic article in accordance with claim 3 wherein said resin-impregnated sheet is enclosed within a moisture-free package and wherein said exposed major surface exhibits a kinetic coefficient of friction of less than about 1.2 while said resin-impregnated sheet is enclosed within said moisture-free package.

45. An orthopedic article in accordance with claim 3, 4, 10, 11, 16, 29, 30, 17, 23, 27, 28, 31, 32, 33, 34, 35, 36, 12, 13, 14, 15, 37, 38, 39, 40, 41, 42, 43, 5, 6, 7, 8, 9, 15, 19, 20, 21, 22, 24, 25, 26, or 44 wherein said exposed major surface of said resin-impregnated sheet exhibits a kinetic coefficient of friction of about 0.93 or less.

46. An orthopedic article in accordance with claim 45 wherein said exposed major surface of said resin-impregnated sheet exhibits a kinetic coefficient of friction of at least about 0.2.

47. An orthopedic article in accordance with claim 3, 4, 10, 11, 16, 29, 30, 17, 23, 27, 28, 31, 32, 33, 34, 35, 36, 12, 13, 14, 15, 37, 38, 39, 40, 41, 42, 43, 5, 6, 7, 8, 9, 15, 19, 20, 21, 22, 24, 25, 26, or 44 wherein said exposed major surface of said resin-impregnated sheet exhibits a kinetic coefficient of friction of about 0.75 or less.

48. An orthopedic article in accordance with claim 47 wherein said exposed major surface of said resin-impregnated sheet exhibits a kinetic coefficient of friction of at least about 0.2.

49. An orthopedic article in accordance with claim 3, 4, 10, 11, 16, 29, 30, 17, 23, 27, 28, 31, 32, 33, 34, 35, 36, 12, 13, 14, 15, 37, 38, 39, 40, 41, 42, 43, 5, 6, 7, 8, 9, 15, 19, 20, 21, 22, 24, 25, 26, or 44 wherein said exposed major surface of said resin-impregnated sheet exhibits a kinetic coefficient of friction of about 0.4 or less.

50. An orthopedic article in accordance with claim 49 wherein said exposed major surface of said resin-impregnated sheet exhibits a kinetic coefficient of friction of at least about 0.2.

51. An orthopedic article in accordance with claim 3, 4, 10, 11, 16, 29, 30, 17, 23, 27, 28, 31, 32, 33, 34, 35, 36, 12, 13, 14, 15, 37, 38, 39, 40, 41, 42, 43, 5, 6, 7, 8, 9, 15, 19, 20, 21, 24, 25, 26, or 44 wherein said exposed major surface of said resin-impregnated sheet exhibits a kinetic coefficient of friction of at least about 0.2.

52. An orthopedic article in accordance with claim 3 wherein two exposed major surfaces of said resin-impregnated sheet are defined by the two sides of said sheet and wherein both of said exposed major surfaces exhibit a kinetic coefficient of friction of less than about 1.2.

53. An orthopedic article in accordance with claim 52 wherein both of said exposed major surfaces of said resin-impregnated sheet exhibit a kinetic coefficient of friction of about 0.93 or less.

54. An orthopedic article in accordance with claim 52 wherein both of said exposed major surfaces of said resin-impregnated sheet exhibit a kinetic coefficient of friction of about 0.75 or less.

55. An orthopedic article in accordance with claim 52 wherein both of said exposed major surfaces of said resin-impregnated sheet exhibit a kinetic coefficient of friction of about 0.4 or less.

56. An orthopedic article in accordance with claim 52, 53, 54, or 55 wherein both of said exposed major surfaces of said resin-impregnated sheet exhibit a kinetic coefficient of friction of at least about 0.2.

57. A method of reducing the tack of an exposed major surface of an orthopedic article comprising a sheet impregnated with a curable and crosslinkable resin, said method comprising depositing a layer of an additive, which is incompatible with the curable and crosslinkable resin, onto the exposed major surface of the resin-impregnated sheet, wherein the additive is present in an amount sufficient to reduce the kinetic coefficient of friction of the exposed major surface of the resin-impregnated sheet to less than about 1.2, wherein said layer is deposited prior to wrapping said resin-impregnated sheet about a substrate, and wherein said resin is not appreciably dispersible in water and adjacent layers of said resin-impregnated sheet are laminatable after immersion in water.

58. A method in accordance with claim 57 wherein the curable resin is comprised of hydrophilic groups covalently bound thereto.

59. A method of preparing an orthopedic article comprising a sheet impregnated with a curable and crosslinkable resin and having reduced tack, the method comprising impregnating the sheet with a mixture comprised of:
(a) the curable and crosslinkable resin, and
(b) an additive which is incompatible with the curable and crosslinkable resin;
wherein the amount of the additive is sufficient to reduce the kinetic coefficient of friction of an exposed major surface of the resin-impregnated sheet to less than about 1.2, and wherein said resin is not appreciably dispersible in water and adjacent layers of said resin-impregnated sheet are laminatable after immersion in water.

60. A method in accordance with claim 59 wherein the curable resin is comprised of hydrophilic groups covalently bound thereto.

* * * * *

UNITED STATES PATENT AND TRADEMARK OFFICE
CERTIFICATE OF CORRECTION

PATENT NO. : 4,774,937
DATED : October 4, 1988
INVENTOR(S) : SCHOLZ et al.

It is certified that error appears in the above-identified patent and that said Letters Patent is hereby corrected as shown below:

On the title page

[75] Inventors, "Wayne E. Larson" should read --Wayne K. Larson--.

[*] Notice, the date "May 22, 2004" should read --May 26, 2004--.

Col. 2, line 41, "tradename" should read --trade name--.

Col. 5, line 66, "tradename" should read --trade name--.

Col. 5, line 67, "tradename" should read --trade name--.

Col. 6, line 14, "shelflife" should read --shelf life--.

Col. 6, line 32, "wter" should be --water--.

Col. 10, line 52, before the word "in" please insert --used--.

Col. 11, line 51, "well suited" should read --well-suited--.

Col. 12, line 42, "shelf-life" should read -- shelf life--.

Col. 13, line 44, "type" should read --tape--.

Col. 15, line 65, "(1/2) lb" should read --(3/4) lb--.

Col. 17, line 47, "cooling" should be --coating--.

UNITED STATES PATENT AND TRADEMARK OFFICE
CERTIFICATE OF CORRECTION

PATENT NO. : 4,774,937

DATED : October 4, 1988

INVENTOR(S) : SCHOLZ et al.

It is certified that error appears in the above-identified patent and that said Letters Patent is hereby corrected as shown below:

Col. 19, line 44, "was" should read --as--.

Col. 22, line 22, please delete comma after "and" and insert comma after --wt/wt--.

Col. 24, line 13, the first occurrence of "in" should read --is--.

Col. 26, line 24, "nonnwoven" should read --nonwoven--.

Col. 26, line 48, delete the second occurrence of "15" and insert --18--.

Col. 26, line 58, please delete the second occurrence of "15" and insert --18--.

Col. 26, line 68, please delete the second occurrence of "15" and insert --18--.

Col. 27, line 10, please delete the second occurrence of "15" and insert --18--.

UNITED STATES PATENT AND TRADEMARK OFFICE
CERTIFICATE OF CORRECTION

PATENT NO. : 4,774,937
DATED : October 4, 1988
INVENTOR(S) : Scholz et al.

It is certified that error appears in the above-identified patent and that said Letters Patent is hereby corrected as shown below:

Col. 27, line 11, after "21," insert --22,--.

Signed and Sealed this

Twenty-eighth Day of March, 1989

Attest:

DONALD J. QUIGG

Attesting Officer

Commissioner of Patents and Trademarks